US010624820B2

(12) United States Patent
Bonderer et al.

(10) Patent No.: US 10,624,820 B2
(45) Date of Patent: Apr. 21, 2020

(54) CERAMIC AND GLASS CERAMIC SLIPS FOR STEREOLITHOGRAPHY

(71) Applicant: Ivoclar Vivadent AG, Schaan (LI)

(72) Inventors: Lorenz Josef Bonderer, Sargans (CH); Jürgen Laubersheimer, Buchs (CH)

(73) Assignee: Ivoclar Vivadent AG, Schaan (LI)

( * ) Notice: Subject to any disclaimer, the term of this patent is extended or adjusted under 35 U.S.C. 154(b) by 42 days.

(21) Appl. No.: 15/753,434

(22) PCT Filed: Sep. 23, 2016

(86) PCT No.: PCT/EP2016/072720
§ 371 (c)(1),
(2) Date: Feb. 19, 2018

(87) PCT Pub. No.: WO2017/050983
PCT Pub. Date: Mar. 30, 2017

(65) Prior Publication Data
US 2018/0243176 A1    Aug. 30, 2018

(30) Foreign Application Priority Data
Sep. 25, 2015   (EP) .................................... 15186958

(51) Int. Cl.
| | |
|---|---|
| *A61K 6/02* | (2006.01) |
| *A61K 6/027* | (2006.01) |
| *A61K 6/00* | (2020.01) |
| *B33Y 70/00* | (2020.01) |
| *B29C 64/188* | (2017.01) |
| *B29C 64/165* | (2017.01) |
| *B28B 1/00* | (2006.01) |
| *B33Y 10/00* | (2015.01) |
| *B33Y 80/00* | (2015.01) |
| *B29K 33/00* | (2006.01) |
| *B29K 509/02* | (2006.01) |
| *B29L 31/00* | (2006.01) |

(52) U.S. Cl.
CPC .......... *A61K 6/0273* (2013.01); *A61K 6/0094* (2013.01); *A61K 6/024* (2013.01); *A61K 6/025* (2013.01); *A61K 6/0215* (2013.01); *A61K 6/0255* (2013.01); *B28B 1/001* (2013.01); *B29C 64/165* (2017.08); *B29C 64/188* (2017.08); *B33Y 70/00* (2014.12); *B29K 2033/08* (2013.01); *B29K 2509/02* (2013.01); *B29L 2031/7536* (2013.01); *B33Y 10/00* (2014.12); *B33Y 80/00* (2014.12)

(58) Field of Classification Search
CPC .. A61K 6/0255; A61K 6/0273; A61K 6/0094; A61K 6/0215; A61K 6/024; A61K 6/025; B33Y 70/00; B29C 64/165; B32B 1/001; B29L 2031/7536
See application file for complete search history.

(56) References Cited

U.S. PATENT DOCUMENTS

| | | | |
|---|---|---|---|
| 4,587,068 A | 5/1986 | Borase et al. | |
| 4,613,560 A | 9/1986 | Dueber et al. | |
| 5,496,682 A | 3/1996 | Quadir et al. | |
| 6,117,612 A | 9/2000 | Halloran et al. | |
| 7,927,538 B2 | 4/2011 | Moszner et al. | |
| 8,133,831 B2 | 3/2012 | Laubersheimer et al. | |
| 9,556,346 B2 | 1/2017 | Suzuki et al. | |
| 2003/0109588 A1 | 6/2003 | Schmidt | |
| 2005/0090575 A1 | 4/2005 | Chaput et al. | |
| 2007/0249770 A1 | 10/2007 | Fukui et al. | |
| 2008/0103226 A1 | 5/2008 | Xu | |
| 2010/0029801 A1* | 2/2010 | Moszner ................ B33Y 70/00 522/167 |
| 2017/0239886 A1 | 8/2017 | Norikane | |

FOREIGN PATENT DOCUMENTS

DE    102005058116 A1    3/2007

OTHER PUBLICATIONS

Gebhardt, A., "Vision Rapid Prototyping," cfi/Ber DKG 83 (2006) No. 13., pp. 7-13.
Gebhardt, A., "Generative manufacturing processes: Rapid Prototyping—Rapid Tooling—Rapid Manufacturing," 3rd Edition, Carl Hanser Verlag, Munich 2007, p. 77.
Beil, A., "Production of micro-components using stereo lithography," Reports from the Institute of Manufacturing Technology and machine tools, University Hannover, Düsseldorf 2002.
Otsu, T. et al., "Role of Initiator-Transfer Agent-Terminator (Iniferter) in Radical Polymerizations: Polymer Design by Organic Disulfides as Iniferters," Makromol. Chem. Rapid Commun. 3, 127-132 (1982).
Elias, H-G., "Macromolecules vol. 1: Chemical Structures and Synthesis," Sixth, completely revised edition, Wiley VCH, pp. 193-197, 1999.
Written Opinion of the International Searching Authority of PCT/EP2016/072720, dated Dec. 22, 2016, 5 pages.

\* cited by examiner

*Primary Examiner* — Edward J Cain
(74) *Attorney, Agent, or Firm* — Ann M. Knab; Thad McMurray (57) ABSTRACT

Slip for the stereolithographic preparation of ceramic or glass ceramic shaped parts which comprises (a) at least one radically polymerizable monomer, (b) at least one photoinitiator, (c) ceramic and/or glass ceramic particles and (d) at least one non-ionic surfactant.

18 Claims, 1 Drawing Sheet

CERAMIC AND GLASS CERAMIC SLIPS FOR STEREOLITHOGRAPHY

CROSS-REFERENCE TO RELATED APPLICATIONS

This application is a National Stage application of International patent application PCT/EP2016/072720 filed on Sep. 23, 2016, which claims priority to European patent application No. 15186958.3 filed on Sep. 25, 2015, all the disclosures of which are incorporated herein by reference in their entirety.

FIELD OF THE INVENTION

The present invention relates to slips for the stereolithographic preparation of ceramic or glass ceramic shaped parts, such as dental inlays, onlays, veneers, crowns, bridges and frameworks.

BACKGROUND OF THE INVENTION

The term "rapid prototyping" (RP) covers generative manufacturing processes in which 3-dimensional models or components are prepared from computer-aided design data (CAD data) (A. Gebhardt, Vision of Rapid. Prototyping, Ber. DKG 83 (2006) 7-12). These are processes such as e.g. stereolithography (SL), selective laser sintering (SLS), 3D printing, fused deposition modelling (FDM), ink-jet printing (IJP), 3D plotting, multi-jet modelling (MJM), solid freeform fabrication (SFF), laminated object manufacturing (LOM), laser powder forming (LPF) and direct ceramic jet printing (DCJP), with which models, components or shaped parts can be prepared cost-effectively even on a small scale (A. Gebhardt, Generative Fertigungsverfahren, 3rd edition, Carl Hanser Verlag, Munich 2007, 77 et seqq.). Stereolithography involves RP processes (A. Beil, Fertigung von Mikro-Bauteilen mittels Stereolithographie, Düsseldorf 2002, VDI-Verlag 3 et segq.) in which a shaped part is constructed in layers from a liquid and curable monomer resin on the basis of CAD data.

Stereolithographic processes for the preparation of dental shaped bodies such as inlays, crowns or bridges are advantageous above all in the case of ceramic materials, because the impression-taking and casting processes, which involve considerable manual outlay in the dental laboratory, and the milling and grinding operations can thus be greatly simplified and at the same time the large loss of material which occurs with non-generative processes can be avoided. As a complete digital process chain is in place today, the standard process steps for the preparation of e.g. multi-unit bridge frameworks (alignment in the articulator, wax modulation, embedding and casting) can be replaced by the digitalization of the model, virtual design of the dental shaped body and generative stereolithographic manufacture thereof.

In the stereolithographic preparation of ceramic shaped parts a ceramic green compact is firstly prepared by layered radiation curing of a free-flowing ceramic slip which is then sintered after the debinding to form a dense ceramic shaped body. The green compact is also called a green body. The elimination of the binder is called debinding. Here, the binder used is usually removed by heating the green compact to a temperature of approx. 80° C. to 600° C. It is essential that the formation of cracks and deformations is avoided as far as possible. The green compact becomes the so-called white body as a result of the debinding. During the debinding, the binder is broken down into volatile components by means of thermal and thermo-chemical processes.

The debinding is a critical step in the process. Here, the danger is high that the component will be damaged by gases which form in the decomposition of the organic matrix and by the pressure exerted by said gases. The danger is particularly high that small defects between the individual construction layers lead, during the debinding, to cracks or even to the complete destruction of the component. This risk can be reduced by increasing the debinding period, which extends the process time greatly, however.

The sintering of the white body takes place in the sintering furnace during high-temperature firing. Thereby, the finely dispersed ceramic powder is compacted and solidified by exposure to a temperature below the melting temperature of the main components, as a result of which the porous component becomes smaller and its strength increases.

U.S. Pat. No. 5,496,682 discloses light-curable compositions for the preparation of three-dimensional bodies by stereolithography, which comprise 40 to 70 vol.-% ceramic or metal particles, 10 to 35 wt.-% monomer, 1 to 10 wt.-% photoinitiator, 1 to 10 wt.-% dispersant and preferably also solvent, plasticizer and coupling agent.

U.S. Pat. No. 6,117,612 describes resins for the stereolithographic preparation of sintered ceramic or metal parts. The resins have a viscosity of less than 3000 mPa·s. For their preparation, monomers with low viscosity are used, preferably in aqueous solution. A high solids content with low viscosity is to be achieved through the use of dispersing agents.

DE 10 2005 058 116 A1 discloses suspensions for the stereolithographic preparation of ceramic implants in the manner described in U.S. Pat. No. 6,117,612 which do not contain diluting agents such as water or organic solvents as the latter are to increase the viscosity through local evaporation when energy is introduced. The viscosity of the suspension is adjusted at less than 20 Pa·s by varying the concentration of a dispersant. Alkyl ammonium salts of copolymers with acid groups are used as dispersants, wherein said dispersants can also be coated onto the particles of the ceramic powder.

Methods and compositions for the stereolithographic preparation of ceramic components are described in US 2005/0090575 A1. It is stated that shaped parts prepared with the liquid materials known from U.S. Pat. No. 5,496,682 are soft and therefore require an additional curing step in order to avoid deformations during firing, while shaped bodies obtained from paste-like materials develop internal stresses during debinding which lead to cracks during sintering. To avoid these problems, plasticizers are used and the quantity of the ceramic powder is chosen such that the viscosity of the compositions is at least 10,000 Pa-s.

From EP 2 233 449 A1, slips for the preparation of ceramic shaped parts by hot-melt inkjet printing processes are known which comprise ceramic particles, wax and at least one radically polymerizable wax and which yield green bodies which can be debound without the formation of cracks. A disadvantage of these slips is that, in the liquid state, they tend to separate on standing for a long time. In the case of hot-melt inkjet processes this is not critical because the slips are only present in liquid form during the printing process, i.e. for a relatively short period of time. However, in the case of stereolithographic processes, the slips must be stable in liquid form over longer periods of time, i.e. in particular, the particles dispersed in the slip must not settle prematurely, which represents a particular problem in respect of the highest possible proportion by volume of ceramic particles in the slip which is sought.

Furthermore, slips for stereolithographic processes are to have a high reactivity and thus enable short exposure times and process times. They must ensure a good green body strength and good dimensional stability, high accuracy and precision after debinding, sintering and final cleaning of the bodies.

SUMMARY OF THE INVENTION

The known slips are not optimal for stereolithographic processes with respect to the above-named requirements. The object of the invention is therefore to provide improved light-curing slips for the stereolithographic preparation of ceramic and glass ceramic shaped parts which satisfy the above requirements and which do not have the named disadvantages. The slips are to be sedimentation-stable in the liquid state in particular. They are to produce green compacts with high green density and strength which can be debound without deformation or the formation of cracks or stresses. On sintering, the green compacts are to lead to high-strength ceramics which are suitable for dental purposes.

BRIEF DESCRIPTION OF THE DRAWINGS

Other advantages, details and characteristics can be seen from the following description and drawings wherein.

DETAILED DESCRIPTION

This object is achieved according to the present invention by slips which comprise
(a) at least one radically polymerizable monomer,
(b) at least one photoinitiator,
(c) ceramic and/or glass ceramic particles and
(d) at least one non-ionic surfactant.

Non-ionic surfactants are substances with surface-active properties which do not form ions in aqueous media. They are molecules which have a hydrophobic and a hydrophilic moiety. The overall hydrophobicity of the molecules can be adjusted by the choice of the length and type of the hydrophobic and hydrophilic moieties.

Slips are preferred which comprise, as non-ionic surfactant (d), a surfactant with a melting point of from 30° C. to 120° C., preferably 40° C. to 100° C., particularly preferably 40° C. to 60° C.

According to the present invention, non-ionic surfactants with an HLB value in the range of from 3 to 16, in particular 4 to 13 and quite particularly of from 4 to 10 are preferred. The HLB value is determined according to Griffin's method.

Preferred non-ionic surfactants (d) are the ethoxylates of fatty alcohols, oxo alcohols or fatty acids, fatty acid esters of sugars and hydrogenated sugars, alkylglycosides as well as block polymers of the ethylene and propylene oxide, in particular short-chain block co-oligomers.

Particularly preferred are fatty acid esters of hydrogenated sugars, in particular those with the formula R'—CO—O-sugar, wherein R' is a branched or preferably straight-chain alkyl radical with 10 to 25 carbon atoms, preferably 12 to 22 carbon atoms. Particularly preferred are straight-chain alkyl radicals with 16 to 22 carbon atoms. "Sugar" means a hydrogenated sugar radical which is preferably ethoxylated 1 to 5 times. Quite particularly preferred are fatty acid esters of sorbitol, in particular sorbitan stearates such as e.g. sorbitan monostearate (CAS 1338-41-6).

A further particularly preferred group of surfactants are ethoxylates of fatty acids, in particular those with the general formula R"—(CO)—(OCH$_2$CH$_2$)$_m$—OH, in which R" is a branched or preferably straight-chain alkyl radical with 10 to 25 carbon atoms, preferably 12 to 22 carbon atoms. Particularly preferred are straight-chain alkyl radicals with 16 to 22 carbon atoms. m is an integer from 2 to 20, preferably 2 to 10 and particularly preferably 2 to 6.

Surfactants which are quite particularly preferred according to the present invention are ethoxylates of fatty alcohols, in particular polyalkylene glycol ethers with the general formula R—(OCH$_2$CH)$_n$—OH, in which R is an alkyl radical with 10 to 20 carbon atoms and n is an integer from 2 to 25. R can be a branched or preferably straight-chain alkyl radical, wherein alkyl radicals with 12 to 22 carbon atoms and in particular straight-chain alkyl radicals with 12 to 22 carbon atoms are preferred. Quite particularly preferred alkyl radicals are lauryl, cetyl, cetearyl and stearyl.

The polyalkylene glycol ethers can be obtained by reacting the corresponding fatty alcohols with ethylene oxide (EO). The index n indicates the number of ethylene oxide radicals. Polyalkylene glycol ethers with 2 to 21 (n=2-21), in particular 2 to 12 (n=2-12) and quite particularly 2 to 5 (n=2-5) ethylene oxide radicals are preferred.

Examples of polyalkylene glycol ethers preferred according to the present invention are compounds in which R is a cetyl radical (C$_{16}$ radical) and n is 20 and in particular 2. These compounds have the INCI designations Ceteth-2 and Ceteth-20. Ceteth-2 has, e.g., the formula C$_{16}$H$_{33}$—(OCH$_2$CH$_2$)$_2$—OH.

Further preferred are compounds in which R is a stearyl radical (C$_{18}$ radical) and n is 2, 10, 20 or 21. These compounds have the INCI designations Steareth-2, Steareth-10, Steareth-20 and Steareth-21. Steareth-2 has, e.g., the formula C$_8$H$_{37}$—(OCH$_2$CH$_2$)$_2$—OH.

Quite particularly preferred non-ionic surfactants are Steareth-20 (HLB=15.3), Steareth-10 (HLB=12.4), Ceteth-20 (HLB=12.9) and in particular Steareth-2 (HLB=4.9) and Ceteth-2 (HLB=5.3).

Mixtures of different non-ionic surfactants and in particular different polyalkylene glycol ethers can likewise be used.

INCI stands for International Nomenclature of Cosmetic Ingredients. This is an international guideline for the correct description of the ingredients in cosmetics. According to the present invention, it was found, completely surprisingly, that the use of non-ionic surfactants which are usually used for the preparation of cosmetic and pharmaceutical products significantly improves the properties of slips for the stereolithographic preparation of ceramic and glass ceramic bodies.

It was found that the non-ionic surfactants used according to the present invention can be mixed homogeneously with radically polymerizable monomers and in particular with acrylates and methacrylates and do not impair the polymerization of these monomers. During the stereolithographic processing of the slips according to the present invention in the liquid state a high reactivity as well as short exposure times and process times can thereby be ensured. It is advantageous that the non-ionic surfactants can also mix well with short-chain polar and strongly reactive monomers.

The slip components are homogeneously miscible above the melting point of component (d) and solidify homogeneously below the melting point of (d). A sedimentation of the ceramic and glass particles is thus effectively prevented below the melting point of component (d). The stability of the mixture is thereby ensured over a long period of time.

The non-ionic surfactants according to the present invention are preferably solid at room temperature. The consequence of this is that they lead to a solidification of the slip, i.e. at room temperature the slips have a paste-like to solid consistency. An advantage of this is that a sedimentation of the ceramic particles is prevented by the homogeneous solidification and thereby the storage stability in the case of storage at room temperature in the solid state is significantly increased. Furthermore, the non-ionic surfactants improve the strength of the polymerized objects (green compacts) at room temperature compared with green compacts made of slips without the constituent (d).

However, it is particularly advantageous that the non-ionic surfactants used according to the present invention also effectively prevent a premature sedimentation of the ceramic and or glass ceramic particles in the liquid state, which results in a high stability of the slips during processing.

As a result of the good dispersion properties of the non-ionic surfactants for ceramic and glass ceramic particles, the slips can additionally be filled with ceramic and/or glass ceramic powder to a significantly higher degree, which results in a higher green density.

A further advantage of the non-ionic surfactants (d) preferred according to the present invention is that they melt on debinding and flow out of the matrix due to their relatively low molecular weight. They do not impair the debinding but rather create channels which promote the discharge of the decomposition products of the organic matrix and thus facilitate the debinding.

If the organic matrix is to be pyrolytically removed ("debinding process") in the case of a polymerized shaped part made of a mixture filled with ceramic particles, during the heating process in the furnace the molecules of the non-ionic surfactant (d) located between the polymer chains will flow out of the shaped body in liquid form before the polymerized portions of the mixture are depolymerized and then pyrolyzed. The risk of defects such as cracks or even the destruction of the shaped body during the debinding process is thereby at least greatly reduced and often completely eliminated. In addition, because component (d) flows out some of the organic material is already removed at a comparatively low temperature, and the further heating process until the complete removal of all organic portions can be carried out easily, whereas hitherto only relatively low heating rates were possible.

The slips according to the present invention produce a good green body strength and high dimensional stability, accuracy and precision after debinding, sintering and cleaning. On sintering, a density of >98% of the theoretical density can be achieved readily.

The slips according to the present invention comprise as monomer (a) at least one (meth)acrylate and/or (meth)acrylamide, preferably mono- or multifunctional (meth)acrylates or mixtures thereof. Materials are particularly preferred which comprise at least one multifunctional (meth)acrylate or a mixture of mono- and multifunctional (meth)acrylates as radically polymerizable monomer. By monofunctional (meth)acrylates is meant compounds with one, by polyfunctional (meth)acrylates is meant compounds with two or more, preferably 2 to 6, radically polymerizable groups.

Examples of particularly suitable mono- or multifunctional (meth)acrylates are methyl, ethyl, 2-hydroxyethyl, butyl, benzyl, tetrahydrofurfuryl or isobornyl (meth)acrylate, p-cumyl-phenoxyethylene glycol methacrylate (CMP-1E), bisphenol A di(meth)acrylate, bis-G(M)A (an addition product of (meth)acrylic acid and bisphenol A diglycidyl ether), ethoxylated or propoxylated bisphenol A di(meth)acrylate, such as e.g. bisphenol A di(meth)acrylate with 3 (SR-348c=methacrylate; SR-349=acrylate, Sartomer) or 2 ethoxy groups (SR-348L=methacrylate, Sartomer), 2,2-bis[4-(2-(meth)acryl-oxypropoxy)phenyl]propane, UD(M)A (an addition product of 2-hydroxyethyl (meth)acrylate and 2,2,4- or 2,4,4-trimethylhexamethylene-1,6-diisocyanate), di-, tri-, tetra-, penta-, hexa- or heptaethylene glycol di(meth)acrylate, di-, tri-, tetra-, penta-, hexa- or heptapropylene glycol di(meth)acrylate, trimethylolpropane tri(meth)acrylate, pentaerythritol tetra(meth)acrylate, as well as glycerol di- and tri(meth)acrylate, 1,4-butanediol di(meth)acrylate, 1,10-decanediol di(meth)acrylate ($D_3MA$), 1,12-dodecanediol di(meth)acrylate or oligomeric polyether, polyester, epoxy, urethane (meth)acrylates and tricyclodecane dimethanol di(meth)acrylate.

Particularly preferred are mono-, di-, trifunctional acrylates and methacrylates with a molecular weight of <1000 g/mol, such as e.g. aliphatic urethane diacrylates, phthalic acid HEA ester (Photomer 4173), pyromellitic acid di-HEA ester (HEA=2-hydroxyethyl acrylate), bisphenol A di(meth)acrylate, bis-G(M)A (an addition product of (meth)acrylic acid and bisphenol A diglycidyl ether), ethoxylated or propoxylated bisphenol A di(meth)acrylate, such as bisphenol A di(meth)acrylate (SR-348c, SR-349, SR-348L), 2,2-bis[4-(2-(meth)acryloxypropoxy)phenyl]-propane, UD(M)A, triethylene glycol di(meth)acrylate (TEGD(M)A), ethoxylated or propoxylated trimethylolpropane tri(meth)acrylate, e.g. 3 mole propoxylated trimethylolpropane triacrylate (Sartomer SR-492) and tripropylene glycol diacrylate. These monomers are characterized by a high reactivity/a high double-bond conversion, good mechanical properties, a low polymerization shrinkage and a relatively low viscosity.

Further suitable monomers are acrylamides such as N-ethyl-acrylamide, N,N-dimethylacrylamide, N-(2-hydroxyethyl)-acrylamide, N,N'-diethyl-1,3-bis (acrylamido)-propane and 1,4-bis(acrylamido)-butane. The bisacrylamides are preferably used in excess compared with the monoacrylamides in the organic binder.

The properties of the slips before and after the light-curing can be influenced by a targeted combination of the monomers. Mixtures of monofunctional and difunctional monomers are characterized by a relatively low viscosity and reactivity of the resin mixture, wherein viscosity and reactivity decrease with the content of monofunctional monomers. A monofunctional monomers content ensures a lower brittleness and a swifter debinding of the green compacts obtained by light-curing of the slips. Mixtures of difunctional and trifunctional monomers have a higher reactivity, wherein the reactivity increases with the trifunctional monomers content. The trifunctional monomers content effects a higher brittleness and slower debinding of the green compacts.

Reactivity and viscosity of the resin mixture as well as the polymerization shrinkage are furthermore determined by the molar mass of the monomers, wherein as the molar mass increases the polymerization shrinkage decreases, while the viscosity rises. Finally, the polarity of the monomers can be used to influence the interaction with the material of the stereolithographic tank, such as e.g. the swelling of the material of the polymerization tank. Silicone elastomers are often used as tank materials. A swelling of silicone elastomers can be largely avoided through the use of OH-group containing monomers.

Preferred photoinitiators (b) for the initiation of the radical photopolymerization are benzophenone, benzoin and derivatives thereof or α-diketones or derivatives thereof, such as 9,10-phenanthrenequinone, 1-phenyl-propane-1,2-dione, diacetyl or 4,4'-dichlorobenzil. Camphorquinone (CQ) and 2,2-dimethoxy-2-phenyl-acetophenone are particularly preferably used and α-diketones in combination with amines as reducing agent are quite particularly preferably used, such as e.g. 4-(dimethylamino)-benzoic acid ester (EDMAB), N,N-dimethylaminoethyl methacrylate, N,N-dimethyl-sym.-xylidine or triethanolamine.

Particularly preferred photoinitiators are Norrish type I photoinitiators, above all monoacyl or bisacyl phosphine oxides, and in particular monoacyltrialkyl- or diacyldialkylgermanium compounds, such as e.g. benzoyltrimethylgermanium, dibenzoyldiethylgermanium or bis(4-methoxybenzoyl)diethylgermanium (MBDEGe). Mixtures of the different photoinitiators can also be used advantageously, such as e.g. bis(4-methoxybenzoyl)diethyl germanium in combination with camphorquinone and 4-dimethylaminobenzoic acid ethyl ester.

Quite particularly preferred are camphorquinone (CAS No. 10373-78-1) in combination with ethyl-4-(dimethylamino)benzoate (EMBO, CAS No. 10287-53-3), as well as Norrish type I photoinitiators, in particular 2,4,6-trimethyl-benzoyldiphenylphosphine oxide (TPO, CAS No. 75980-60-8), ethyl(2,4,6-trimethylbenzoyl)phenyl-phosphinate (TPO-L, CAS No. 84434-11-7), phenylbis(2,4,6-trimethylbenzoyl)phosphine oxide (Irgacure 819, CAS 162881-26-7), bis(2,6-difluoro-3-(1-hydropyrrol-1-yl)phenyl)titanocene (Irgacure 784, CAS No. 125051-32-3), 2-benzyl-2-(dimethylamino)-4'-morpholinobutyrophenone (Irgacure 369, CAS No. 119313-12-1), 1-butanone-2-(dimethylamino)-2-(4-methylphenyl)methyl-1-4-(4-morpholinyl)phenyl (Irgacure 379, CAS-No. 119344-86-4) and quite particularly bis(4-methoxybenzoyl)diethylgermanium (MBDEGe; K69).

The slips according to the present invention comprise ceramic and/or glass ceramic particles as component (c).

By ceramics is meant inorganic materials which have a crystalline structure and are usually prepared from corresponding powders. The preparation of the ceramic preferably takes place by sintering (sintered ceramic). Oxide ceramics are preferably obtained by sintering metal oxide powders such as e.g. $ZrO_2$ or $Al_2O_3$. In addition, oxide ceramics can also comprise one or more glass phases.

Preferred are ceramic particles based on $ZrO_2$ or $Al_2O_3$, preferably pure $ZrO_2$ or pure $Al_2O_3$, particles based on $ZrO_2$ stabilized with $HfO_2$, CaO, $YO_2O_3$, $CeO_2$ and/or MgO, particles based on other metal oxides as well as ceramic composite materials which are prepared from several oxides and are thus constructed from different crystalline oxide phases, preferably ZrO—$Al_3O_3$, in particular pure $ZrO_2$—$Al_2O_3$ or $ZrO_2$—$AlO_3$ stabilized with $HfO_2$, CaO, $Y_2O_3$, $CeO_2$ and/or MgO.

The term "pure" is to be understood to mean "chemically pure", i.e. a $ZrO_2$ or $Al_2O_3$ ceramic is constructed only from $ZrO_2$ or $Al_2O_3$ respectively. In addition to the base oxide such as $ZrO_2$ or $Al_2O_3$, stabilized ceramics comprise a stabilizer which is preferably selected from $HfO_2$, CaO, $YO_3$, $CeO_2$, MgO and mixtures thereof. The stabilizer is preferably used in a quantity of from 3 to 5 wt.-%, relative to the mass of the stabilized ceramic. High-strength $ZrO_2$ ceramics preferably comprise 3 to 5 wt.-% $Y_2O_3$ (yttrium oxide) to stabilize the tetragonal crystal structure. This $ZrO_2$ ceramic is called Y-TZP (yttrium-stabilized tetragonal zirconium dioxide polycrystals). Ceramic particles which contain only base oxide and stabilizer are particularly preferred.

According to the present invention, slips are preferred which comprise glass ceramic particles as component (c). Glass ceramics are materials which are usually prepared from amorphous glasses, in particular silicate glasses, by controlled crystallization and in which a glass phase and one or more crystal phases are present simultaneously in the solid. In the case of glass ceramics, both glass powders and also glass ceramic powders can be used as a starting point. Glass ceramic particles which comprise leucite crystals are particularly preferred and those which comprise lithium disilicate crystals are quite particularly preferred. These can be prepared advantageously from lithium disilicate glass powder, without crystallite moieties, by thermal treatment (crystallization firing and sintering).

The ceramic or glass ceramic particles used as component (c) are preferably coloured. For this, the ceramic and/or glass ceramic particles are preferably mixed with one or more pigments. Inorganic pigments, such as for example the oxides of Pr, Tb, Ce, Co, Ni, Cu, Bi, La, Nd, Sm, Eu, Gd and in particular of Fe, Mn, Cr, Er are particularly preferred. Coloured spinel compounds of the type $AB_2O_4$, wherein A is preferably an alkali metal ion or an alkaline earth metal ion and B is a transition metal ion of a higher oxidation state than A, can also be used advantageously to colour the ceramic or glass ceramic powder. The spinels are particularly suitable for colouring glass ceramic and in particular lithium disilicate glass ceramic. The chromophoric components are added in a quantity which is required in order to achieve the desired coloration. The type and quantity of the chromophoric component(s) are preferably chosen such that tooth-coloured ceramic shaped parts are obtained after the debinding and sintering. The colour impression is only finally formed during the sintering. The chromophoric components are usually used in a quantity of in each case 0.01 to 1 wt.-%, preferably 0.05 to 0.5 wt.-% relative to the total mass of component (c).

To achieve the desired colour impression, it is also possible to use mixtures of differently coloured ceramic or glass ceramic powders.

The particle size of component (c) is preferably in the range of from 10 nm to 100 μm, preferably 100 nm to 10 μm. It depends on the ceramic used. In the case of $Al_2O_3$, the size of the particles used as component B is preferably in the range of from 50 to 500 nm, particularly preferably between 75 and 200 nm; in the case of glass ceramic in the range of from 500 nm to 50 μm, quite preferably between 1 and 10 μm; in the case of TZP-3Y zirconium dioxide in the range of from 50 to 500 nm, quite preferably between 50 and 350 nm. The particle size is preferably chosen such that sedimentation-stable slips are obtained. The particle sizes are the absolute upper and lower limits.

Furthermore, ceramic or glass ceramic particles with a particle size in the range of 10-200 nm can also be used as nano- or organosols, i.e. as a dispersion of the nanoparticles in a solvent, in a suitable monomer of component (a) or in a mixture thereof.

According to a particularly preferred embodiment of the invention, the particles of component (c) are surface-modified with suitable substances. Those compounds which are chemically bonded, i.e. by ionic or covalent bonds, to the surface of the ceramic or glass ceramic particles are preferably used for the surface modification. Compounds which contain either acid groups, preferably carboxylic acid, phosphonic acid, hydrogen phosphate groups or acidic phosphoric acid ester groups, or silyl groups, preferably alkoxysilyl groups, are preferred. The particle surface can be partially or preferably completely covered with the modification agent. The modification agents used according to the present invention are monomeric compounds.

Those compounds which, unlike the so-called adhesion promoters or coupling reagents, contain groups which only react with the particle surface but not radically polymerizable groups, which form a covalent bond with the resin matrix (a), are particularly suitable according to the present invention. Here, such compounds are called non-polymerizable surface modification agents. These compounds have the advantage that a stable bond does not form between the ceramic particle surface and the polymer matrix in the cured green compact, which simplifies the complete removal of the polymer portions in the debinding process.

Linear or branched carboxylic acids, such as e.g. formic acid, acetic acid, propionic acid, octanoic acid, isobutyric acid, isovaleric acid, pivalic acid or phosphonic acids, e.g. such as methyl-, ethyl-, propyl-, butyl-, hexyl-, octyl- or phenylphosphonic acid are particularly suitable as non-polymerizable surface modification agents. Silanes which are suitable as non-polymerizable surface modifiers are, for example, propyltrimethoxysilane, phenyltrimethoxysilane, hexyltrimethoxysilane, octyltrimethoxysilane, trimethylchlorosilane, trimethylbromosilane, trimethylmethoxysilane or hexamethyldisilazane. Acidic phosphoric acid esters, such as e.g. dimethyl, diethyl, dipropyl, dibutyl, dipentyl, dihexyl, dioctyl or di(2-ethylhexyl) phosphate are quite particularly preferred.

Suitable surface modification agents for aqueous slips are furthermore polymers, in particular polyelectrolytes, e.g. polycarboxylic acids or polycarboxylic acid salts, or non-ionic polymers, such as e.g. polyethylene glycol or carboxymethylcellulose. Polyelectrolytes, which carry ionic groups, such as e.g. ammonium polycarboxylate, can adsorb onto the surface of solids relatively easily and can thereby impart an electric charge to the particles. In the case of organic, non-aqueous slips polymers which are soluble in the polyreaction resin are suitable. Modification agents with a molar mass in the range of from 50 to 5,000 g/mol are preferred.

Surface modification agents are optionally used in a quantity of preferably 0.1 to 5 wt.-%, particularly preferably 0.2 to 2 wt.-% and quite particularly preferably 0.5 to 1.5 wt.-% relative to the mass of the slip.

In addition to the above-named components, the slips according to the present invention preferably comprise in addition at least one additive which is selected from dyes, solvents, inhibitors, debinding accelerators, defoaming agents and/or antiskinning agents.

Organic dyes are preferred as dye, in particular azo dyes, carbonyl dyes, cyanine dyes, azomethines and methines, phthalocyanines and dioxazines. Dyes which are soluble in the slip, in particular azo dyes, are particularly preferred. A quite particularly preferred dye is (4-(4-nitrophenylazo) aniline (Disperse Orange 3, CAS No. 730-40-5). Those substances are preferred as chromophoric component (e) which absorb in the same wavelength range as the polymerization initiator. Dyes are particularly preferred which have an absorption maximum which corresponds to the wavelength of the light used for the curing. Dyes with an absorption maximum in the range of from 350 to 550 nm, preferably 380 to 480 nm are very advantageous.

Unlike in the case of the chromophoric components used to colour the ceramic or glass ceramic powder, by dyes is meant here those substances which completely combust on debinding and sintering. These dyes only serve to colour the slip and thus to facilitate the processing thereof. They do not serve to colour the ceramic.

Organic solvents are preferred as solvent, in particular those solvents which have a boiling temperature of at least approx. 120° C., preferably of from 150 to 250° C., with the result that a premature evaporation does not occur during the stereolithographic processing of the slip. Mixtures of those solvents which can be progressively evaporated in a temperature range between 150 and 250° C. are particularly suitable. Quite particularly suitable are n-octanol, triethylene glycol divinyl ether, 2-amino-2-methyl-1-propanol, 2-methyl-2,4-pentanediol, tripropylene glycol, tetraethylene glycol, triethylene glycol, triethyl citrate, acetoacetic acid ethyl ester, cyclohexanol, cyclohexanone, diethylene glycol monomethyl ether, oxalic acid dibutyl ester, 2,5-dimethoxytetrahydrofuran, polyethylene glycol 300, 1- or 2-nonanol, diethylene glycol diethyl ether, and mixtures thereof.

Preferred solvents are furthermore polyethylene glycols (PEG), polypropylene glycols (PPG), PEG-PPG co-polymers, glycerol and glycerol derivatives, i.e. in particular ethoxylated and/or propoxylated glycerol, as well as phthalates. Particularly preferred are solvents with an Mw smaller than 5,000 g/mol, preferably smaller than 1,000 g/mol. Compounds which are liquid at room temperature and which do not react with the other components of the slip under storage conditions and conditions of use are suitable as solvents. Particularly preferred solvents are PEG 200-600 g/mol, PPG 200-800 g/mol, co-PEG-PPG 200-800 g/mol and in particular polypropylene glycol ~400 g/mol. Mixtures of these solvents can also be used advantageously.

The solvent(s) are preferably used in a total quantity of from 0 to 50 wt.-%, particularly preferably of from 5 to 20 wt.-%, relative to the mass of the slip.

It was found that the evaporation of the above solvent additionally promotes the formation of micropores in the green compact. Just as the channels formed by the outflow of the non-ionic surfactants, these pores close on sintering. They facilitate the escape of the gases during the debinding and thus prevent the formation of stresses and cracks. Furthermore, the danger of a separation of the stereolithographically produced layers is reduced and a complete removal of all of the organic components is promoted.

Alternatively, the porosity of the green compact can also be increased by extractive removal of elutable portions before the heat treatment. Suitable extractable components are water-soluble polymers such as e.g. polyvinyl alcohol, polyvinyl pyrrolidone and polyethylene glycols. Furthermore, benzine-soluble substances such as e.g. long-chained fatty acid esters can be used. The preferred quantity of extractable components is between 0 and 30 wt.-%, particularly preferably between 1 and 20 wt.-%, relative to the mass of the slip.

The slips according to the present invention can advantageously comprise, as stabilizer, an inhibitor to prevent a spontaneous polyreaction as further additive. The inhibitors or stabilizers improve the storage stability of the slips and also prevent an uncontrolled polyreaction in the stereolithographic tank. The inhibitors are preferably added in such a quantity that the slips are storage-stable over a period of approx. 2-3 years. The inhibitors are particularly preferably used in a quantity of from 0.001 to 1.0 wt.-%, quite particularly preferably 0.001 to 0.50 wt.-%, in each case relative to the overall mass of the slip.

Phenols such as hydroquinone monomethyl ether (MEHQ) or 2,6-di-tert.-butyl-4-methyl-phenol (BHT), which are really effective only in the presence of oxygen and are preferably used in a concentration range of 100-2000 ppmw are preferably used as so-called aerobic inhibitors.

Suitable anaerobic inhibitors are phenothiazine, 2,2,6,6-tetramethyl-piperidine-1-oxyl radical (TEMPO), iodine and copper(I) iodide. These are already effective in low concentrations of preferably 10-50 ppm even in the absence of oxygen. A polymerization only takes place when these additives are used up. It is advantageous to use a mixture of aerobic and anaerobic inhibitors.

Aerobic inhibitors are preferably used in a quantity of from 0.001 to 0.50 wt.-% and anaerobic inhibitors in a quantity of from 0.001 to 0.02 wt.-%, in each case relative to the total mass of the slip. Preferred mixtures comprise 0.005-0.10 wt.-% aerobic inhibitors and 0.001 to 0.01 wt.-% anaerobic inhibitors, likewise relative to the total mass of the slip.

According to a further embodiment of the invention, the slips comprise a so-called debinding accelerator as additional additive. The latter is preferably used in a quantity of from 0 to 20 wt.-%, particularly preferably 0.01 to 10 wt.-%, in each case relative to the total mass of the slip. By debinding accelerators is meant substances which facilitate the removal of the binder during the debinding process.

The debinding of the green compact can be promoted or influenced in a targeted manner e.g. by polyreactively active substances in the polyreaction resin. These are, on the one hand, additives which influence the network formation, such as above all chain-transfer-active substances, so-called chain regulators, which lead to a reduction in the polymer network density and thus to a better thermal decomposability. Known chain regulators e.g. for radical polymerization are above all mercaptans, such as e.g. lauryl mercaptan, and disulphides. Disulphides, above all dithiourethane disulphides, such as e.g. tetramethylthiuram disulphide or isopropylxanthogenic acid disulphide, act as so-called photoiniferters in the radical photopolymerization. These are compounds which both act as photoinitiator (photoini-) and also participate in transfer reactions (-fer-) and termination reactions (-ter) (cf. T. Ostsu, M. Yoshida, Makromol. Chem., Rapid. Commun. 3 (1982) 127-132: Role of Initiator-Transfer Agent-Terminator (Iniferter) in Radical Polymerizations: Polymer Design by Organic Disulfides as Iniferters). The addition of chain-transfer-active substances, i.e. of chain regulators or photoiniferters, effects a reduction of the network density of the polyreaction network with a virtually unchanged reactivity of the polyreaction resin mixture. Chain regulators and photoiniferters are preferably used in each case in a quantity of from 0.005 to 25 wt.-% and particularly preferably 0.01 to 10 wt.-%, relative to component (a).

Comonomers which lead to a reduction in the thermal stability of polymer networks can also be used as debinding accelerators. Comonomers which contain thermally labile groups, such as e.g. peroxide, azo or urethane groups, which are incorporated into the polymer network during the stereolithographic process and then accelerate the decomposition of the polymer network in the thermal debinding process are suitable for this. A preferred example of a polymerizable peroxide is 4,4'-divinyl benzoyl peroxide which can be obtained by reaction of 4-vinyl benzoyl chloride with sodium peroxide. A preferred example of a polymerizable azo compound is the ester from 2-hydroxyethyl methacrylate and 4,4'-azobis-(4-cyanovaleric acid). Preferred thermally labile urethanes can be obtained from diisocyanates, for example by reaction of 2,2,4-trimethylhexamethylene diisocyanate (TMDI) or toluylene diisocyanate (TDI) with hydroxypropyl acrylate (HPA) or 2-hydroxyethyl acrylate (HEA). A further example of a thermally labile monomer building block is $\alpha,\alpha,\alpha',\alpha'$-tetramethyl-1,4-benzene-dimethyl acrylate, the incorporation of which into a Michael addition network for example of diacrylates and diacetoacetates in the presence of catalytic amounts of acid leads to an accelerated decomposition of the polymer network.

Furthermore, comonomers, the polyreaction products of which can be easily thermally decomposed, are suitable as debinding accelerators. Comonomers which, like α-methylstyrene, have a low ceiling temperature T, are preferred for radical polymerization resins. The ceiling temperature is the limit temperature at which the polymerization is in equilibrium with the depolymerization, and can be calculated from the quotient of the polymerization enthalpy and the polymerization entropy (cf. H.-G. Elias, Makromolekile, vol. 1, 6th edition, Wiley-VCH, Weinheim etc. 1999, 193 et seqq.). For example, $T_c$ for α-methylstyrene is 61° C. The ceiling temperature $T_c$ of polytetrahydrofuran (PTHF) is 80° C. Accordingly, the decomposability of poly(meth)acrylate networks can be accelerated e.g. by using telechels, in particular PTHF di(meth)acrylate telechels as comonomer. According to the present invention, comonomers with a ceiling temperature of from −10 to 150° C., preferably 10 to 150° C. and particularly preferably 20 to 130° C. are particularly suitable. The comonomers are preferably used in a quantity of from 0.1 to 30 wt.-% and particularly preferably 0.5 to 20 wt.-%, relative to component (a).

Furthermore, the slips according to the present invention can comprise additives which promote the oxidative decomposition of the polymer matrix during the debinding process, such as e.g. peroxides, which are stable at room temperature, or catalytically active components which allow for a catalytic debinding. In addition to peroxides, other substances which have an oxidizing effect, such as e.g. nitric acid, or which release or form oxidizing agents, are also suitable.

In addition, the slips according to the present invention can comprise defoaming agents and/or antiskinning agents which prevent foaming during the preparation of the slips and the formation of a skin during the processing of the slips respectively. Defoaming and/or antiskinning agents are preferably used in each case in the organic matrix in a quantity of from 0 to 5 wt.-%, particularly preferably 0.1 to 2 wt.-%, relative to the mass of component (A).

The rheological properties of the slips according to the present invention are preferably adjusted such that their viscosity is in the range of 200-20,000 mPas, particularly preferably 500-5,000 mPas. The viscosity is determined with a plate-plate viscometer at the desired processing temperature of the slip. The processing temperature is preferably in the range of 30-100° C., particularly preferably 40-70° C.

The slips according to the present invention preferably have the following composition:
- 5 to 65 wt.-%, preferably 9 to 57 wt.-%, particularly preferably 10 to 40 wt.-% monomer (a);
- 0.001 to 1.0 wt.-%, preferably 0.01 to 1.0 wt.-%, particularly preferably 0.1 to 1.0 wt.-% photoinitiator (b);
- 33 to 90 wt.-%, preferably 40 to 88 wt.-%, particularly preferably 56 to 86 wt.-% ceramic and/or glass ceramic particles (c); 1 to 30 wt.-%, preferably 2 to 15 wt.-%, particularly preferably 3 to 10 wt.-% non-ionic surfactant (d).

The slips preferably also comprise:
- 0 to 0.2 wt.-%, preferably 0 to 0.05 wt.-%, particularly preferably 0 to 0.02 wt.-% dye(s) for colouring the slips; and/or
- 0.1 to 5 wt.-%, preferably 0.2 to 2 wt.-%, particularly preferably 0.5 to 1.5 wt.-% surface modification agent; and/or 0 to 50 wt.-%, preferably 5 to 20 wt.-%, particularly preferably 5 to 10 wt.-% solvent.

Unless otherwise indicated, all details relate to the total weight of the slip. The chromophoric components used to colour the ceramic or glass ceramic particles are contained in the quantities named for component (c).

The slips according to the present invention are particularly suitable for the preparation of ceramic or glass ceramic shaped parts, in particular for the preparation of dental restorations, such as e.g. inlays, onlays, veneers, crowns, bridges or frameworks.

A subject of the invention is furthermore a process for the preparation of ceramic or glass ceramic shaped parts in which (A) a green compact is prepared by curing a slip according to the present invention by local introduction of radiation energy accompanied by the formation of the geometric shape of the green compact,
(B) the green compact is then subjected to a heat treatment to remove the binder (debinding), in order to obtain a white body, and
(C) the white body is then sintered.

The green compact is prepared in step (A) by stereolithography. By layered radiation curing of a ceramic slip which is free-flowing at the processing temperature, a ceramic green compact is prepared, which is debound in step (B). The binder used is removed here by heating the green compact to a temperature of preferably 90° C. to 600° C., and the so-called white body is obtained. The white body is sintered in step (C) to form a dense ceramic shaped body. The sintering of the white body is carried out in a sintering furnace, preferably at a temperature for glass ceramics of from 650 to 1100° C., preferably 700 to 900° C., for zirconium dioxide of from 1100 to 1600° C. and for aluminium oxide of from 1400 to 1800° C., preferably 1600 to 1700° C. The ceramic shaped bodies prepared according to the process according to the present invention are characterized by a high strength and great accuracy of detail. The bending strength according to ISO 6872 is preferably more than 100 MPa, in particular in the range of from 150 to 500 MPa, for shaped bodies made of glass ceramic. Shaped bodies made of $Al_2O_3$ have a bending strength of preferably more than 300 MPa, in particular of from 500 to 700 MPa and shaped bodies made of $ZrO_2$ of more than 500 MPa, in particular of from 800 to 1100 MPa.

The invention is explained illustrated in more detail below with reference to drawings and examples.

Figure 1:
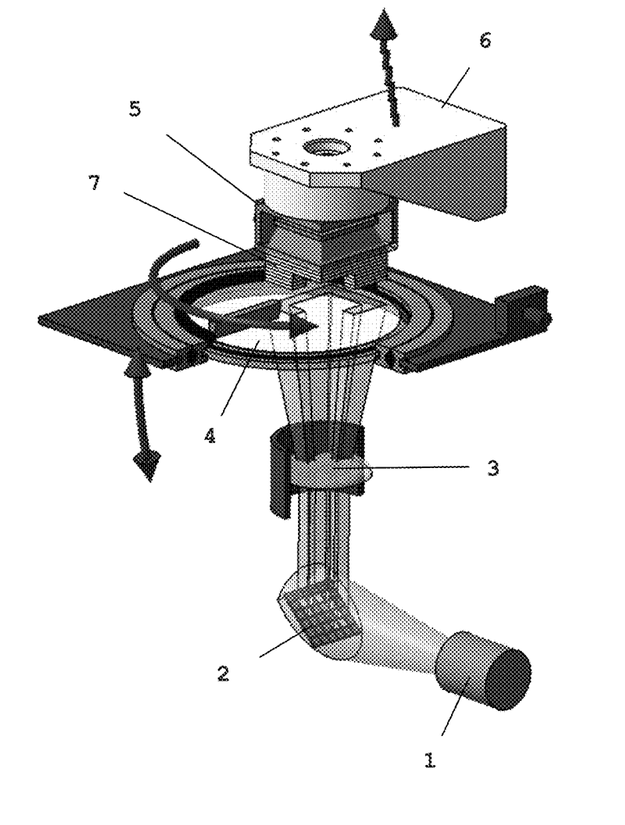
FIG. 1 shows a schematic representation of a device for carrying out the process according to the present invention.

FIG. 1 shows a schematic representation of a device for carrying out the process according to the present invention. As FIG. 1 shows, the device comprises a container 4 for the slip according to the present invention. The container 4 is also called polymerization tank or tank. In the embodiment shown, the tank 4 has a transparent window through which the slip is selectively illuminated and cured from below. A computer-controlled DMD chip (Digital Mirror Device) 2, which is irradiated with a light source 1, is arranged below the tank 4. The image of the mirror 2 is projected onto the transparent window in the base of the container 4 by an optical device 3. Arranged above the tank 4 is a substrate carrier 6 movable in Z direction which carries the body 7 constructed in layers. The substrate carrier 6 has a carrier plate 5. The carrier plate 5 is immersed in the slip until the distance between the carrier plate 5, or the body 7 attached thereto, and the inner surface of the tank 4 corresponds to the layer thickness of the layer to be produced. The slip layer between carrier plate and inner tank surface is then selectively illuminated and cured through the transparent window with the help of the DMD chip 2. Cured areas form which adhere to the carrier plate 5. The carrier 6 is then raised in Z direction, with the result that a slip layer with the desired thickness forms again between the adhering layer and the inner tank surface. This layer is also selectively cured by renewed illumination and the desired shaped body, preferably a dental restoration, is constructed in layers by repeating the process.

EXAMPLES

Example 1

Lithium Disilicate Slips

Except for the glass ceramic particles, the components listed in Table 1 were weighed out and stirred at 50° C. until all of the components had dissolved. The powder component (c) was then added in 2-3 batches. After each addition of powder, the slip was homogenized in a Hauschild Speedmixer DAC 400fvz at 2750 rpm for 2 min. The total weight of the slip was in each case approx. 50-100 g.

| Component | Substance | Slip 1 | Slip 2 | Slip 3*) |
|---|---|---|---|---|
| Monomer (a) | 3 mole propoxylated trimethylolpropane triacrylate[1] | 8.65% | 8% | 8.65% |
| Monomer (a) | UDMA (RM3) | 6.8% | 6% | 6.8% |
| Initiator (b) | Ivocerin[2] | 0.05% | 0.05% | 0.05% |
| Non-ionic surfactant (d) | Steareth-2[3] | 9.15% | 3.9% | — |
| Dye | 4-(4-Nitrophenylazo)aniline 3[4] | 0.005% | 0.005% | 0.005% |
| Dispersant | Phosphoric acid ester[5] | 1% | 1% | 1% |
| Solvent | Polypropylene glycol (400 g/mol) | — | 6.7% | 9.15% |
| Glass ceramic particles (c) | Lithium disilicate[6] | 74.345% | 74.345% | 74.345% |

*)Comparison example
[1]SR492 (Sartomer)
[2]Bis(4-methoxybenzoyl)diethylgermanium
[3]Brij S2 (Croda Europe Ltd, England)
[4]Disperse Orange 3 (Sigma-Aldrich; CAS No. 730-40-5)
[5]Solplus D540 (CAS No. 1000871-74-8; Lubrizol)
[6]Lithium disilicate glass ceramic (e.max Transpa; Ivoclar Vivadent, Liechtenstein), ground; D50 = 6 μm Slips 1 to 3 are lithium disilicate slips. Slip 1 does not contain any solvent. Solvent (PPG400) is additionally present in slip 2 and the content of non-ionic surfactant (d) is reduced. The slip is thus less sensitive to temperature fluctuations during processing but in return is less solid and is softer at room temperature. Slip 3 (comparison example) does not contain any non-ionic surfactant.

The non-ionic surfactant effects a solidification of the slip at room temperature, whereby the storage stability is increased significantly. After 3 weeks, no sedimentation and no phase separation could be seen in the case of slips 1 and 2. Slip 3 clearly sedimented within 3 weeks and a clearly visible transparent liquid film formed on the surface. The sedimented slip could not be re-homogenized by manual shaking or stirring and could also only be re-homogenized to a limited extent by intensive machine stirring (Speedmixer). These possibilities are, however, not possible on the SL device.

Example 2

Wax-Containing Slips (Comparison Example)

| Component | Quantity | Proportion |
|---|---|---|
| ZrO$_2$ particles | 150 g | (35.7 vol.-%; 78.2 wt.-%) |
| Paraffin wax | 20.310 g | (32.7 vol.-%; 10.6 wt.-%) |
| PPG700DA | 11.858 g | (16.8 vol.-%; 6.2 wt.-%) |
| 5-DAMS | 5.442 g | (7.7 vol.-%; 2.8 wt.-%) |
| Octadecene | 2.020 g | (3.7 vol.-%; 1.1 wt.-%) |
| Hypermer LP-1 | 2.000 g | (3.2 vol.-%; 1.0 wt.-%) |
| TEMPO | 0.001 g | (0.03 vol.-%; 5 wt.-ppm) |
| Photoinitiator | 0.300 g | (0.017 vol.-%; 0.15 wt.-%) |

Key:
ZrO$_2$ TZ-3YS-E (commercial grade) from Tosoh Corporation, Tokyo, JP (ZrO$_2$ stabilized with Y$_2$O$_3$, primary particle size 300-350 nm)
Paraffin wax Melting point 54-56° C., viscosity (at 80° C. and at a shear rate of 1000 s$^{-1}$) 3-4 mPa · s (Siliplast; Zschimmer & Schwarz, Lahnstein, DE; contains in total approx. 0.5% emulsifier)
Hypermer LP-1 Surface modification agent based on a medium-chain polyester (Uniqema, GB.)
PPG700DA Polypropylene glycol 700 diacrylate
5-DAMS Pentaerythritol diacrylate monostearate
TEMPO 2,2,6,6-Tetramethylpiperidinyloxyl
Photoinitiator Bis-(4-methoxybenzoyl)diethylgermanium Preparation of the Slip:

The wax, the monomers PPG700DA and 5-DAMS, and the surface modification agent were introduced at 70° C. into a dissolver (Dispermat®, VMA-Getzmann GmbH, Reichshof, DE). The ZrO$_2$ powder was added portionwise at low rotation speeds. Once all of the powder had been incorporated, the rotation speed was increased to 20,000 min$^{-1}$ and mixing was carried out for at least 30 min. The heating occurring because of the high shear forces in the system made any external heating unnecessary, and under certain circumstances cooling may actually be necessary. After the 30 min. of intensive stirring, the slip was cooled while being gently stirred. As long as the slip was still liquid, octadecene and TEMPO were added, as well as the photoinitiator at the end.

Example 3

Preparation of Shaped Bodies

The prepared slip was converted into cylindrical test pieces with a diameter of 6 mm and a height of 6 mm in a self-built Digital Light Processing (DLP) stereolithography unit (Blueprinter, TU Vienna). The slip temperature was set to approx. 60° C. It is important that the slip and all of the components (in particular the components which come into contact with the layer to be formed) are heated to a temperature above the melting point of component (d). The wavelength of the light was 460 nm and the slips were illuminated with 150 mJ/cm$^2$ per layer. The distance between the layers was set to 25 μm.

After the construction, the parts were removed manually from the construction platform, cleaned in an ultrasonic bath in an aqueous washing-up liquid solution at 50° C. for 5-10 minutes and then blown dry. The temperature of the cleaning solution was above the melting point of component (d).

After the drying, the cleaned components were debound in a laboratory furnace (Nabertherm GmbH, Germany). The debinding program used for cylinders with a diameter of 6 mm and a height of 6 mm was: (i) heating from room temperature to 100° C. in 2 h 40 min.; (ii) further heating to 200° C. in 6 h 40 min.; (iii) then further heating to 420° C. in 7 h 20 min.; (iv) maintaining at 420° C. for 1 h. In the case of larger and thicker components, corresponding adaptations are necessary. A good circulation of air must be maintained in the furnace chamber throughout the entire debinding process so that the formed gases can be effectively removed.

At the start of the debinding, pores formed as a result of the evaporation of the solvent and the outflow of the non-ionic surfactant. In the case of slip 1, primarily the non-ionic surfactant (d) was responsible for the formation of the porosity. These pores make it easier for the formed gases to escape and defect-free white bodies were obtained which could be sintered without problems.

Thereafter, the green bodies were completely debound and could be dense-sintered in a sintering furnace (Programat P510, Ivoclar Vivadent) in a standard manner. The sintering program was: 10 K/min. to 700° C., 30 min. holding time at 700° C., 10 K/min. to 850° C., vacuum from 500° C., 1 min. holding at 850° C., cooling at (10 K/min.) to 700° C., approx. 90 min.

The photopolymerization of the slip from Example 2 proceeded slowly in the stereolithography process because of the low reactivity of the long-chained monomers and yielded a green body with low mechanical stability which required extremely careful handling. The printed objects were very fragile and sensitive also after the debinding.

The invention claimed is:

1. Slip for stereolithographic preparation of ceramic or glass ceramic shaped parts, wherein said slip comprises
    (a) at least one radically polymerizable monomer,
    (b) at least one photoinitiator and
    (c) ceramic and/or glass ceramic particles,
    characterized in that said slip comprises
    (d) at least one non-ionic surfactant, wherein said slip comprises as non-ionic surfactant (d)
        a fatty acid ester of hydrogenated sugars with the formula R'—CO—O-sugar in which R' is a branched or straight-chain alkyl radical with 10 to 25 carbon atoms and "sugar" means a hydrogenated sugar radical which is ethoxylated 1 to 5 times or not ethoxylated, and/or
        a fatty acid ethoxylate of the general formula R"—(CO)—(OCH$_2$CH$_2$)$_m$—OH in which R" is a branched or straight-chain alkyl radical with 10 to 25 carbon atoms and m is an integer from 2 to 20, and/or
        a polyalkylene glycol ether with the general formula R—(OCH$_2$CH$_2$)$_n$—OH in which R is an alkyl radical with 10 to 20 carbon atoms and n is an integer from 2 to 25.

2. Slip according to claim 1, wherein said slip comprises as non-ionic surfactant (d), a surfactant with a melting point of from 30° C. to 120° C.

3. Slip according to claim 1, wherein said slip comprises as non-ionic surfactant a surfactant with an HLB value of from 3 to 16.

4. Slip according to claim 1, wherein said slip comprises as monomer (a) at least one (meth)acrylate and/or (meth)acrylamide.

5. Slip according to claim 1, wherein said slip comprises as component (c) ceramic particles based on ZrO$_2$, Al$_2$O$_3$ or $ZrO_2$—$Al_2O_3$, or based on $ZrO_2$, $Al_2O_3$, $ZrO_2$—$Al_2O_3$ which is stabilized in each case with $HfO_2$, CaO, $Y_2O_3$, $CeO_2$ and/or MgO.

6. Slip according to claim 1, wherein said slip comprises as component (c) glass ceramic particles based on leucite, apatite and/or lithium disilicate glass ceramic.

7. Slip according to claim 1, wherein the particles of component (c) have a particle size in the range of from 10 nm to 100 µm.

8. Slip according to claim 1, wherein said slip additionally comprises at least one surface modification agent and/or at least one additive which is selected from dyes, solvents, inhibitors, debinding accelerators, defoaming agents and/or antiskinning agents.

9. Slip according to claim 8, wherein
the surface modification agent is selected from linear or branched carboxylic acids, formic acid, acetic acid, propionic acid, octanoic acid, isobutyric acid, isovaleric acid, pivalic acid, phosphoric acids, methyl-, ethyl-, propyl-, butyl-, hexyl-, octyl- or phenylphosphonic acid, propyltrimethoxysilane, phenyltrimethoxysilane, hexyltrimethoxysilane, octyltrimethoxysilane, trimethylchlorosilane, trimethylbromosilane, trimethylmethoxysilane or hexamethyldisilazane, acidic phosphoric acid esters, dimethyl, diethyl, dipropyl, dibutyl, dipentyl, dihexyl, dioctyl or di(2-ethylhexyl) phosphate; and/or
the dye is selected from organic dyes comprising azo dyes, carbonyl dyes, cyanine dyes, azomethine, methine, phthalocyanine, dioxazine, (4-(4-nitrophenylazo)aniline or a mixture thereof; and/or
the solvent is selected from polyethylene glycols, polypropylene glycols, PEG-PPG co-polymers, glycerol and glycerol derivatives, phthalates, PEG 200-600 g/mol, PPG 200-800 g/mol, co-PEG-PPG 200-800 g/mol and polypropylene glycol ~400 g/mol and mixtures thereof.

10. Slip according to claim 1 comprising
5 to 65 wt.-% monomer (a);
0.001 to 1.0 wt.-% photoinitiator (b);
33 to 90 wt.-% ceramic and/or glass ceramic particles (c);
1 to 30 wt.-% non-ionic surfactant (d).

11. Process of using the slip according to claim 1 for the preparation of ceramic or glass ceramic dental restorative shaped parts comprising an inlay, onlay, veneer, crown, bridge or framework.

12. Process for the preparation of a ceramic or glass ceramic shaped part, wherein
(A) a green compact is prepared by curing a slip according to claim 1 by local introduction of radiation energy accompanied by the formation of the geometric shape of the green compact,
(B) the green compact is then subjected to a heat treatment to remove the binder (debinding), in order to obtain a white body, and
(C) the white body is sintered.

13. Slip according to claim 2, wherein the melting point of the non-ionic surfactant (d), is in the range of 40° C. to 100° C.

14. Slip according to claim 3, wherein the HLB value of the non-ionic surfactant is in the range of 4 to 13.

15. Slip according to claim 10 comprising
9 to 57 wt.-% monomer (a);
0.01 to 1.0 wt.-%, wt.-% photoinitiator (b);
40 to 88 wt.-% ceramic and/or glass ceramic particles (c);
2 to 15 wt.-% non-ionic surfactant (d).

16. Slip according to claim 10 comprising
10 to 40 wt.-% monomer (a);
0.1 to 1.0 wt.-% photoinitiator (b);
56 to 86 wt.-% ceramic and/or glass ceramic particles (c);
3 to 10 wt.-% non-ionic surfactant (d).

17. Slip according to claim 2, wherein the melting point of the non-ionic surfactant (d), is in the range of 40° C. to 60° C.

18. Slip according to claim 3, wherein the HLB value of the non-ionic surfactant is in the range of 4 to 10.

* * * * *